United States Patent [19]
Phillips

[11] Patent Number: 6,071,313
[45] Date of Patent: *Jun. 6, 2000

[54] SPLIT FOOT PROSTHESIS

[76] Inventor: Van L. Phillips, 5499 Maravillas, P.O. Box 1873, Rancho Santa Fe, Calif. 92067

[ * ] Notice: This patent is subject to a terminal disclaimer.

[21] Appl. No.: 09/083,296

[22] Filed: May 22, 1998

Related U.S. Application Data

[63] Continuation-in-part of application No. 08/789,159, Jan. 24, 1997, Pat. No. 5,776,205, which is a continuation of application No. 08/643,869, May 7, 1996, abandoned, which is a continuation of application No. 08/185,325, Jan. 21, 1994, Pat. No. 5,514,185, which is a continuation of application No. 08/091,458, Jul. 14, 1993, abandoned, which is a continuation of application No. 07/936,854, Aug. 27, 1992, abandoned, which is a continuation of application No. 07/662,928, Feb. 28, 1991, Pat. No. 5,181,933.

[51] Int. Cl.[7] ................................................. A61F 2/66

[52] U.S. Cl. ........................................................... 623/55

[58] Field of Search ........................................ 623/53–56

[56] References Cited

U.S. PATENT DOCUMENTS

| | | |
|---|---|---|
| Re. 1,908 | 3/1865 | Parmelee . |
| 43,031 | 6/1864 | Kirschmann . |
| 61,780 | 2/1867 | Watson . |
| 65,187 | 5/1867 | Emery . |
| 428,839 | 5/1890 | Gault . |
| 546,405 | 9/1895 | Marks et al. . |
| 951,989 | 3/1910 | Hanger . |
| 961,582 | 6/1910 | Bradley et al. . |
| 1,071,230 | 8/1913 | Hanger . |
| 1,294,632 | 2/1919 | Dickson . |
| 1,424,264 | 8/1922 | Shrodes . |
| 1,502,593 | 7/1924 | Shrodes . |
| 1,804,915 | 5/1931 | Collins . |

(List continued on next page.)

FOREIGN PATENT DOCUMENTS

| | | |
|---|---|---|
| 583917 | 1/1925 | France . |
| 295807 | 12/1916 | Germany ................................. 623/55 |
| 325171 | 9/1920 | Germany . |
| 883321 | 7/1953 | Germany . |
| 963849 | 5/1957 | Germany . |
| 1498490 | 11/1987 | U.S.S.R. . |
| 306313 | 2/1929 | United Kingdom . |

OTHER PUBLICATIONS

JPO: Journal of Prosthetics and Orthotics, vol. 8, No. 2, Spring 1996—"Cirrus from Second Nature" (p. 11A).
Cirrus Second Nature Brochure.
College Park Introduces the TruStep Foot Brochure.
FootNotes, Dec. 1990 "New Foam Cover has Appeal for Wearers and Prosthetists Alike" (two pages).
Technical Bulleton, No. 2, 1996 "Flex–Foot Product Updates Effective Sep. 1996" (one page).
Brochure by Ohio Willow Wood Company, entitled Carbon Copy System III, Recreating the Human Leg.
Brochure by Flex–Foot, Inc., entitled Introducing The Air–Flex Lower Limb Prosthesis.
Brochure by Flex–Foot, Inc., entitled The New Modular III Flex–Foot and Flex–Walk II.
Brochure by Model Instrument Development, entitled The Seattle Lightfoot.

*Primary Examiner*—David H. Willse
*Attorney, Agent, or Firm*—Knobbe, Martens, Olson & Bear, LLP

[57] ABSTRACT

A prosthetic foot is characterized by an ankle portion and a foot portion. The foot portion extends from heel to toe and is secured to a downwardly extending lower attachment section of the ankle portion. The foot portion and part of the ankle portion are bifurcated into multiple side-by-side foot portions such that they are capable of movement independent from one another. Preferably, the foot is bifurcated by the provision of a slot in said foot and ankle portions. A strap or similar expedient may be provided to limit the movement of the side-by-side foot portions relative to each other, if desired.

28 Claims, 4 Drawing Sheets

U.S. PATENT DOCUMENTS

| | | |
|---|---|---|
| 2,036,830 | 4/1936 | Rowley . |
| 2,197,093 | 4/1940 | Campbell . |
| 2,440,075 | 4/1948 | Campbell . |
| 2,453,969 | 11/1948 | Carter . |
| 2,475,372 | 7/1949 | Catranis . |
| 2,475,373 | 7/1949 | Catranis . |
| 2,619,652 | 12/1952 | Vesper . |
| 3,335,428 | 8/1967 | Gajdos . |
| 3,754,286 | 8/1973 | Ryan . |
| 4,306,320 | 12/1981 | Delp . |
| 4,328,594 | 5/1982 | Campbell et al. . |
| 4,506,395 | 3/1985 | Haüpt . |
| 4,547,913 | 10/1985 | Phillips . |
| 4,570,926 | 2/1986 | Ensmenger . |
| 4,636,220 | 1/1987 | Ziegelmeyer . |
| 4,645,509 | 2/1987 | Poggi et al. . |
| 4,676,801 | 6/1987 | Landeen . |
| 4,718,913 | 1/1988 | Voisin . |
| 4,721,510 | 1/1988 | Cooper et al. . |
| 4,822,363 | 4/1989 | Phillips . |
| 4,865,612 | 9/1989 | Arbogast et al. . |
| 4,892,553 | 1/1990 | Prahl . |
| 4,892,554 | 1/1990 | Robinson . |
| 4,938,776 | 7/1990 | Masinter . |
| 4,959,073 | 9/1990 | Merlette . |
| 4,991,317 | 2/1991 | Lakic . |
| 5,037,444 | 8/1991 | Phillips . |
| 5,062,859 | 11/1991 | Naeder . |
| 5,066,305 | 11/1991 | Firth . |
| 5,112,356 | 5/1992 | Harris et al. . |
| 5,116,383 | 5/1992 | Shorter et al. . |
| 5,116,384 | 5/1992 | Wilson et al. . |
| 5,139,525 | 8/1992 | Kristinsson . |
| 5,181,933 | 1/1993 | Phillips . |
| 5,258,038 | 11/1993 | Robinson et al. . |
| 5,258,039 | 11/1993 | Goh et al. . |
| 5,443,527 | 8/1995 | Wilson . |
| 5,443,528 | 8/1995 | Allen . |
| 5,514,185 | 5/1996 | Phillips . |
| 5,571,210 | 11/1996 | Lindh . |
| 5,776,205 | 7/1998 | Phillips . |

SPLIT FOOT PROSTHESIS

RELATED APPLICATIONS

This application is a continuation in part of U.S. patent application Ser. No. 08/789,159, filed Jan. 24, 1997, now U.S. Pat. No. 5,776,205, which is a continuation of U.S. patent application Ser. No. 08/643,869, filed May 7, 1996 now abandoned, which is a continuation of U.S. patent application Ser. No. 08/185,325, filed Jan. 21, 1994, now U.S. Pat. No. 5,514,185, which is a continuation of U.S. patent application Ser. No. 08/091,458, filed Jul. 14, 1993, now abandoned, which is a continuation of U.S. patent application Ser. No. 07/936,854, filed Aug. 27, 1992, now abandoned, which is a continuation of U.S. patent application Ser. No. 07/662,928, filed Feb. 28, 1991, now U.S. Pat. No. 5,181, 933.

BACKGROUND OF THE INVENTION

This invention relates to foot prostheses in general, and specifically to a split foot prosthesis which incorporates a plurality of curvilinear foot portions which cooperate with one another to provide the wearer with performance characteristics not available from prior art prosthesis.

A number of prosthetic devices have attempted to provide energy-storing-and-releasing functions to simulate ambulation on a natural limb. For example, see my U.S. Pat. No. 4,547,913 for my invention relating to a "Composite Prosthetic Foot and Leg," and U.S. Pat. No. 4,822,363 for my invention relating to a "Modular Composite Prosthetic Foot and Leg." Also, my U.S. Pat. No. 5,037,444, discloses prosthetic foot devices with similar preferred materials and methods of manufacture, and with corresponding benefits therefrom.

Each of my aforementioned inventions is characterized by lightweight, elongated structures incorporating polymer impregnation of superimposed reinforcing laminae maintained in the desired configuration. Such configurations and constructions provide the desirable characteristics of strength and flexibility in the prosthetic member, and achieve a simulation of the performance of natural feet which had previously not been attainable. Such prostheses may be provided in modular assemblies, whereby the particular performance characteristics of a given prosthesis may be adapted and readily adjusted to meet the needs and activity level of the individual patient.

Other prosthetic foot devices include U.S. Pat. No. 3,335, 428 to Gajdos, which attempts to duplicate the skeletal and skin structure of a natural human foot, U.S. Pat. No. 2,075, 583 to Lange, which incorporates a rubber form mounted in operative relationship with a rigid metallic core, and U.S. Pat. No. 4,645,509 to Poggi, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

Although several of the aforementioned prostheses have provided flexure in a fore-and-aft direction, such prior art devices are relatively stiff and unresponsive with respect to torsional loading which might result from leaning to one side or from ambulation in a direction other than straight ahead. In fact, such prostheses provide a consistent energy response for loading at any given fore-and-aft location on the prosthesis, regardless of whether the loading occurs at one edge of the prosthesis or at the center thereof.

OBJECTS AND ADVANTAGES OF THE INVENTION

It is, therefore, an object of my invention to provide a prosthetic foot which overcomes some or all of these limitations by providing a prosthetic foot having varying energy-absorbing and energy-storing performance dependent upon the lateral location of the contact between the foot and an underlying supporting surface, as well as the angle of impact therebetween. In particular, the prosthesis of my invention includes a plurality of foot portions capable of independent movement of one another.

In a preferred embodiment, as described below, the foot portions are fabricated by providing a slot through virtually the entire prosthesis, effectively dividing it into two independent prostheses. When both of these independent portions are similarly loaded and stressed, such as during straight-ahead walking, the portions cooperate and act in unison to achieve a performance similar to a foot with no division therein. When the prosthesis of my invention undergoes lateral loading, however, the various portions may act independently from one another and thereby provide performance characteristics which may vary substantially from those of a foot with no division.

In effect, the prosthesis of my invention simulates the sideways turning of a natural ankle, in that it permits the energy-storing structure of the entire foot to twist slightly from side to side in response to various loading conditions.

Moreover, such independent movement provides additional effective contact area between the bottom of the prosthesis and a confronting supporting surface, under the aforementioned lateral loading conditions. Instead of a single outer edge of the prosthesis contacting the supporting surface, two or more "edges" may achieve such contact, improving the traction or frictional interaction of the prosthesis on the surface.

Another object of my invention is the provision of a prosthetic foot of the aforementioned character which includes connecting or retaining means such as a strap for limiting the movement of the relevant independent foot portions, or selected ones of them, with respect to one another. This insures that the energy-storing capabilities of the entire foot are utilized when the foot is placed under conditions of extreme lateral stresses. In such situations, the connecting means effectively connects selected sections of the foot portions with a predetermined amount of play therebetween, whereby after one of the connected portions has been displaced that predetermined distance with respect to the other, the strap will require that both connected portions be simultaneously actuated in order for further displacement in that direction to occur.

It is a further object of my invention to provide a prosthetic foot of the aforementioned character which is of modular configuration, resulting in ready assembly and adjustability thereof. The foot of my invention preferably includes forefoot and heel portions that can be readily exchanged with correspondingly-constructed forefoot and heel portions to provide size adjustment or different spring rates to suit the size of foot of the amputee or the stride, height, weight, and activity level of the amputee. Therefore, a range of combinations of spring rate and size can be provided to the amputee, achieving a natural stride and resilience of gait.

Another object of the invention is the provision of a prosthetic foot of the aforementioned character in which the forefoot and heel portions of the prosthesis are fabricated from superimposed laminates maintained in operative relationship by an encapsulating polymer, and further in which said foot is susceptible to bending stress determined by the number of the laminates and polymers in the respective element. Thus, the laminates are encapsulated in a polymer and capable of spring stress response as loads are imposed thereupon during the utilization of said foot.

A further object of the invention is the provision of a prosthetic foot of the aforementioned character which consists of continuous, integrally and simultaneously formed attachment, ankle, arch and toe sections of a forefoot portion, and attachment and heel sections of a heel portion, said sections being respectively fabricated as unitary structures by polymer impregnation of superimposed reinforcing laminae maintained in the desired configuration of said foot and said sections being capable of spring stress generated energy storage whereby the subjection of the prosthetic foot to bending moments will cause uniform transmission of spring stress through said sections of said foot.

The polymers utilized to encapsulate the fibrous laminae are characterized by elasticity and flexibility so that the foot prosthesis deflects proportionally to the engagement of said prosthetic foot with an adjacent surface, causing the resultant energy to be stored and subsequently released when the gait of the amputee incorporating thrust and lift components results in the utilization of the stored energy and a consequent reduction of the energy expended by the amputee.

In order to impart a cosmetic aspect to the prosthetic foot, and after proper fitting of the foot to insure that it is properly balanced and of appropriate size, the prosthesis may be encapsulated in a suitably shaped cosmetic shroud. The shroud must be sufficiently flexible so as not to inhibit the free movement and flexure of the foot, but, because of the inherently resilient and stress-absorbing characteristics of said foot little dependence is needed upon the ancillary cushioning action of the shroud.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein. All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

DETAILED DESCRIPTION OF THE PREFERRED EMBODIMENT

Figure 4:
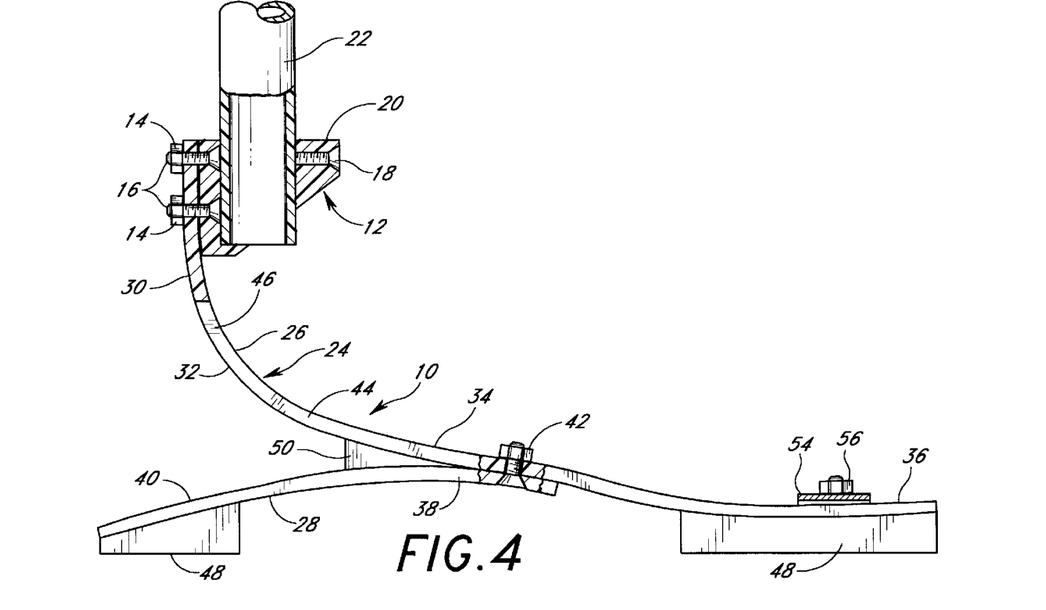
FIG. 4 is a partially cutaway side elevation sectional view of the prosthesis of FIG. 1, taken along line 4—4.
Figure 5:
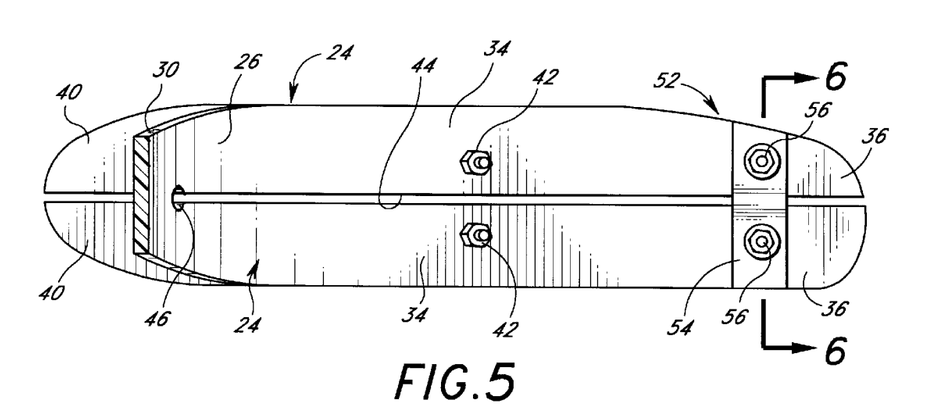
FIG. 5 is a partially sectional plan view of the prosthesis of FIG. 1 taken along line 5—5 of FIG. 3.
Figure 6:
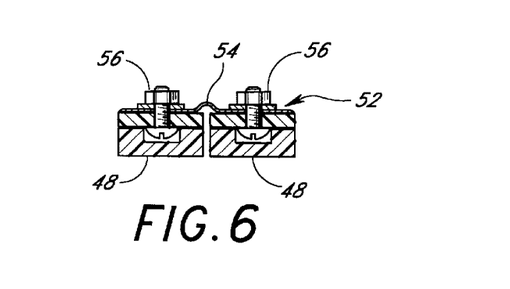
FIG. 6 is a sectional view of the prosthesis of FIG. 1, taken along line 6—6 of FIG. 5.

Referring to the drawings, and particularly to FIG. 4 thereof, I show a preferred embodiment of a foot prosthesis 10 constructed in accordance with the teachings of the invention and including attachment means 12 such as cooperating nuts 14, bolts 16, set screw 18, pylon 22 and coupling 20 for facilitating the operative engagement of the foot with a wearer's stump. Attached to the attachment means 12 and extending downwardly therefrom is a plurality of curvilinear foot portions 24, shown in the preferred embodiment as a bifurcated forefoot portion 26 and heel portions 28 secured thereto.

The foot portions 24 such as the preferred forefoot portion 26 further preferably include an attachment section 30, a curvilinear ankle section 32, FIG. 4, an arch section 34 and a toe section 36. The heel portions 28 preferably include an attachment section 38 and a heel section 40 projecting rearwardly therefrom.

It should be noted that the anatomical terms such as toe, ankle, arch, heel and the like, are used herein for convenience only in referencing various components and portions of the prosthesis described herein. It should be understood by those skilled in the art that these terms are not to be construed narrowly as requiring duplication of the function or structure of naturally occurring toes, ankle, arch or heels, but should be construed broadly as referring only to the location of such structures as illustrated in the drawings.

The various sections of the forefoot and heel portion, respectively, are preferably formed integrally with one another and simultaneously by the incorporation of a plurality of laminae embedded in a hardened, flexible polymer, similar to the fabrication methods taught in my above-noted patents. The forefoot and heel portions of my invention, as well as the inventions of my above-noted patents, may also be manufactured by various other expedients, including injection molding and/or the use of thermoplastic materials and processes, or any of a range of combinations thereof.

Among other things, chopped fiber may be blended in a thermoplastic or thermoset resin and the resulting mixture injection molded into an appropriate configuration. Alternatively or additionally, thermoplastic laminae may be wound around an injection-molded core, or a thermoplastic resin may be injected between thermoplastic or thermoset laminae, whereby the laminates are bonded onto the injected material.

Figure 1:
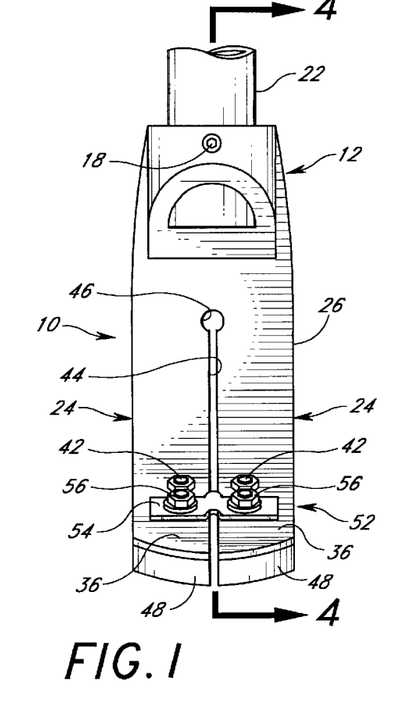
FIG. 1 is a front elevation view of a prosthesis constructed in accordance with one embodiment of the invention.
Figure 2:
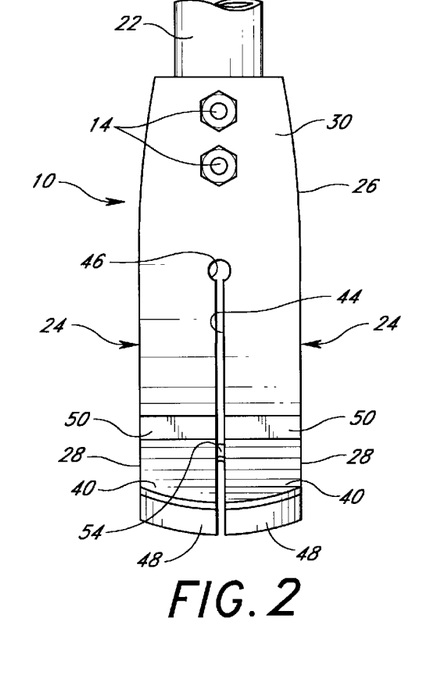
FIG. 2 is a rear elevation view of the prosthesis of FIG. 1.
Figure 3:
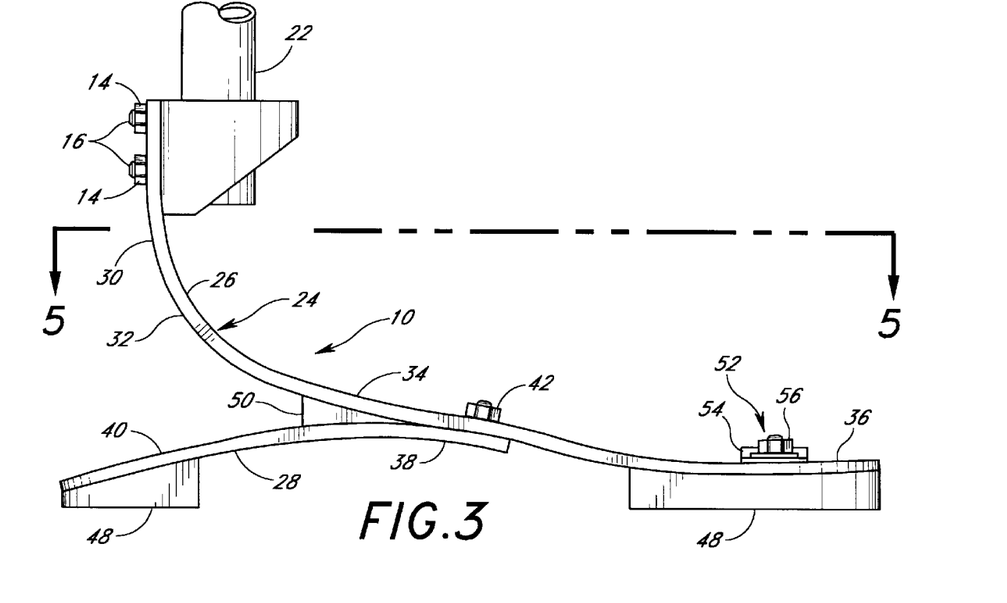
FIG. 3 is a side elevation view of the prosthesis of FIG. 1.

The attachment section 38 of the heel portions 28 are preferably secured to corresponding intersections of the curvilinear ankle sections 32 and the arch sections 34 of the curvilinear foot portions 24. Such securement may be permanent, through simultaneous and integral fabrication or through the use of epoxy, glue or the like, or may be demountable, FIGS. 3 and 4, through the utilization of bolt, nut and washer combinations 42 assembled through corresponding holes in the forefoot and heel portions 26 and 28. Demountable attachment is preferred, in that it permits forefoot portions to be selectably matched with any of various heel portions having different spring rates, as more fully discussed below.

As indicated above, the forefoot and heel portions 26 and 28 are preferably fabricated from superimposed laminates maintained in operative relationship by an encapsulating polymer and susceptible to bending stress determined by the thickness of the laminates. Preferred materials and fabrication process are more thoroughly described and explained in my U.S. Pat. Nos. 4,547,913 and 4,822,363. These may include laminates such as carbon fibers and/or fiberglass or synthetic fibers such as Kevlar. Exemplary alternative methods and materials are described hereinabove.

As illustrated in the accompanying Figures, the forefoot portion 26 is preferably bifurcated into two foot portions 24, although additional multiple portions 24 (not shown) may be beneficially provided and utilized without departing from the scope of my invention.

Such bifurcation or further division may be accomplished through the incorporation of a slot 44 along the complete or substantially the complete length of the prosthesis 10. Such a slot 44 may be molded or subsequently cut into the prosthesis, or may be achieved by the juxtaposition of two or more completely separate foot portions 24 (not shown), each of which would be operatively attached to the attachment means 12. If the slot 44 is molded or cut into a single forefoot portion 26, stress relief means 46, such as a hole, is preferably provided at the upper end of the slot 44, to prevent undesired excessive loading and deterioration of the prosthesis at that location. Such a hole may be drilled or molded into the prosthesis.

The prosthesis of my invention is also preferably provided with underlying pads 48 and lever action blocks 50, as described in my aforementioned patents and pending applications. Such pad members may be affixed to the underside of the forefoot and heel portions, to create a profile for the bottom of the prosthesis 10 which corresponds to the interior of a shoe. Such a profile orients the foot 10, when the foot is in an unstressed state, at an appropriate angle for wearing shoes.

Additionally, the preferred embodiment of my invention includes retaining or connecting means 52 such as a strap 54 operatively attached to selected sections of the curvilinear foot portions 24 through the provision of nut, bolt and washer combinations 56 or the like. The strap 54 is preferably fabricated from impregnated canvas or other flexible, lightweight, tough material, and is located remote from the attachment section 30. By providing some play in the strap 54 rather than utilizing a taut strap, the selected foot portions 24 may flex independently of each other while exposed to lateral loading conditions, but will flex in a coordinated manner after sufficient movement has occurred to draw the strap taut. Thus, in extreme lateral loading conditions, more than one foot portion 24 will function to absorb and exert energy and prevent overload of a single foot portion 24.

It will be obvious to those skilled in the art that a virtually infinite variety of forefoot portions 26 and heel portions 28 may be fabricated, each having unique spring stress response characteristics determined by the configuration, composition and amount of the various component materials utilized therein. The aforementioned demountable connections of the heel portion to the forefoot portion therefore permits interchangeability of those portions to match the weight, stride and activity schedule of the wearer utilizing the prosthetic foot.

Those skilled in the art will understand that attachment means 12 have been described hereinabove merely by way of example, and that many alternative attachment means are available and may be utilized without departing from the scope of the invention, including without limitation, temporary or permanent bonding using various adhesives, plugs, pyramid connectors and/or the like.

The attachment section or sections 30, when assembled with the attachment means 12, are substantially rigid and capable of sustaining torsional, impact, and other loads impressed thereupon by the wearer during use of the foot 10. In addition, the inherent rigidity of the attachment section or sections prevents them from being distorted in any way and causes the effective transmission of the aforesaid loads imposed thereupon between the wearer and the prosthetic foot 10.

The forefoot and heel portions 26 and 28 can be provided with different numbers of laminates to make them more or less compliant to loads transmitted between the wearer and the surface upon which the foot 10 is impacting. Consequently, when confronted with various anomalies in an amputee, such as an overweight condition or excess activity levels, the structure of the forefoot and heel portions can be materially modified to provide action which is precisely adjusted to the needs of the amputee. Moreover, a variety of forefoot and heel portions 26 and 28 can be made available to an amputee, allowing the flexibility of the prosthesis to be adjusted on the basis of the particular activity which the amputee is undertaking.

In the preferred embodiment, the forefoot and heel portions 26 and 28 are constructed with some slight tapering of thickness along the length thereof, although those skilled in the art will understand that the invention is not limited to such tapering construction.

The materials from which the portions 26 and 28 are fabricated are preferably such as to provide an energy-storing, resilient, spring-like effect. This is because each engagement of the prosthetic foot 10 with an adjacent surface impresses compression, torsional, and other loads upon the prosthesis which must be stored within the prosthesis and then, dependent upon the stride of the wearer, be reimpressed upon said surface to achieve a natural stride conforming, ideally, in all respects to the stride of the unimpaired limb of the wearer of the prosthesis 10.

The multi-portioned prosthesis of my invention thus provides a compliance to lateral stresses and loading not previously achievable, and accomplishes this desirable result in a light-weight and responsive prosthesis. Moreover, the modularity of the invention permits the performance characteristics of the prosthesis to be fine-tuned and adjusted to the particular weight, size and activity of the wearer.

As previously mentioned, the attachment section 30, the ankle section 32, the arch section 34, and the toe section 36 of the forefoot portion 26 are preferably formed integrally. Likewise, the attachment section 38 and the heel section 30 of the heel portion 28 are preferably formed integrally. The configuration of these sections allows bending and compressive loads imposed during impingement of the prosthetic foot 10 upon an adjacent surface to be absorbed and subsequently reimposed upon said surface. These various sections are so designed that they function, substantially, to permit some flexure of the portions 26 and 28. In combination with the multiple foot portions 24, the prosthesis 10 functions in manner analogous to a normal foot and normal ankle joint, permitting the wearer to experience a more natural gait and feel with the prosthesis than was possible with prior art prostheses.

The prosthetic foot of my invention can thus be provided in different sizes to correspond to the size of the natural foot of the wearer of the prosthesis 10. When such different sizes are provided, corresponding reduction or increase in the number of laminae and thickness of taper if any, of the respective sections of the forefoot and heel portions 26 and 28 can be made to provide for the proper flexure of said sections.

Moreover, the flexibility of the prosthetic foot of my invention may be further increased, while still maintaining acceptable strength characteristics, by providing an auxiliary ankle member or an auxiliary forefoot portion (not shown, but similar to that illustrated in my U.S. Pat. No. 5,181,932). Such an auxiliary member or portion would be operatively affixed to the forefoot portions 26 to provide some relative movement therebetween.

The aforementioned flexure of the various foot portions 24 provides the capacity for increased surface area contact between the bottom of the prosthesis 10 and a confronting supporting surface during both the impact and delivery phases of lateral loading of the prosthesis 10. Instead of a single edge of the prosthesis effectively contacting the supporting surface, the above-described independent flexure of the portions 24 permits corresponding edges of each such portion 24 to contact the supporting surface, thereby improving the traction or frictional contact between the bottom of the prosthesis and the confronting surface.

Figure 10:
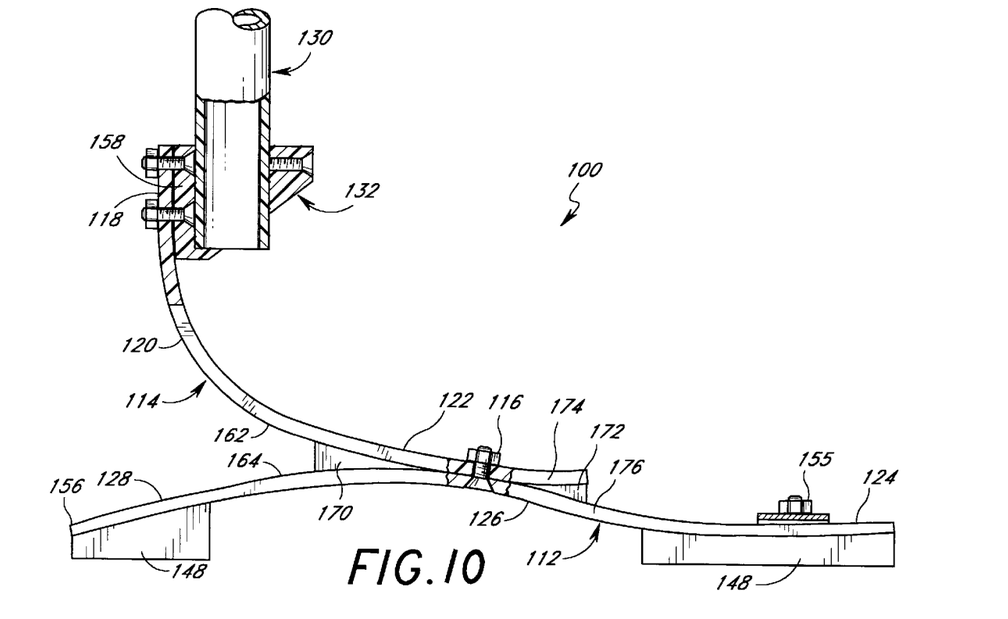
FIG. 10 is a partially cut away side elevation sectional view of the prosthesis of FIG. 7, taken along line 10—10.

Referring to the drawings, and particularly to FIG. 10 thereof, I show a foot prosthesis 100 constructed in accordance with an alternative embodiment of the invention and including a foot portion 112 and an ankle portion 114 operatively and demountably connected to each other by bolt and nut combinations 116. Alternatively, if desired, the foot and ankle portions can be permanently or demountably secured to each other, such as by epoxy adhesive, an intermediate resilient member, or the like. The ankle portion 114 of the prosthesis 100 includes a substantially rigid upper attachment section 118 (FIG. 10) a curvilinear ankle section 120, and a lower attachment section 122. The sections 118, 120 and 122 of the ankle portion 114 are formed integrally with one another and simultaneously by a plurality of juxtaposed, shaped laminae imbedded in a hardened, flexible polymer.

The attachment section 118 has a rearward surface 158, as shown in FIG. 10, and a forward surface substantially parallel thereto. The attachment section 118 is substantially rigid and capable of sustaining torsional, impact and other loads impressed thereupon by the foot portion 112 and ankle portion 114 of the prosthesis 100. In addition, the inherent rigidity of the attachment section 118 prevents it from being distorted in any way and causes the effective transmission of the aforesaid loads imposed thereupon to a suitable ancillary prosthetic pylon 130, through a pylon coupling 132, constructed of graphite or some other appropriately strong material.

Figure 9:
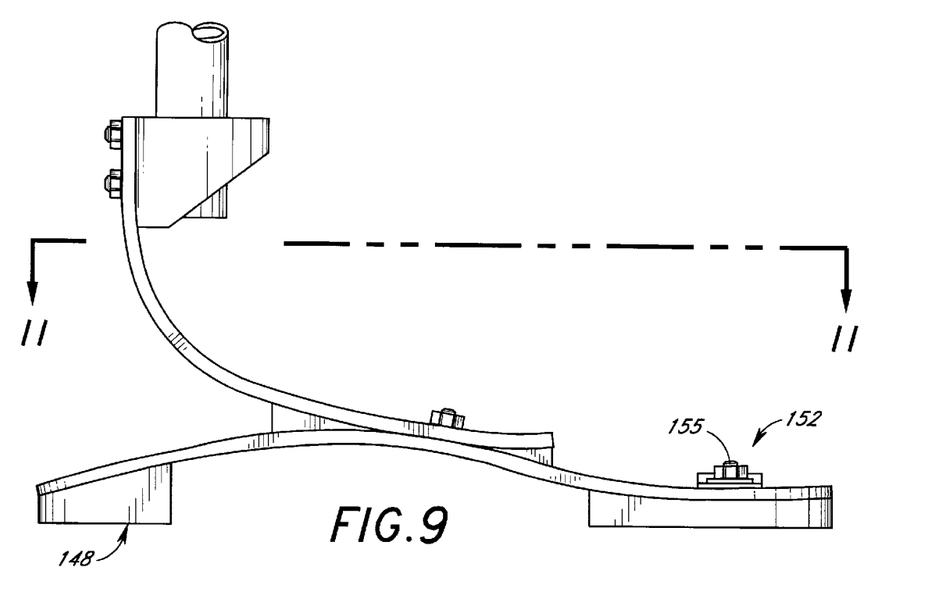
FIG. 9 is a side elevation view of the prosthesis of FIG. 7.

The bolt and nut combinations 116, in conjunction with optional load distributing metallic plates (not shown), serve to secure the ankle portion 114 in operative relationship with the foot portion 112 of the prosthesis 100, as best shown in FIGS. 9 and 10 of the drawings. This mode of demountable securement of a selected ankle portion 114 in operative relationship with a selected foot portion 112 of the prosthesis 100, advantageously permits a wide range of different sized feet and stress load response characteristics to be related to each other to accomplish the optimum functional correspondence between a foot and ankle portions 112 and 114 to accommodate to the maximum extent possible the needs of the wearer of the prosthesis, and also, to provide for a proper mating of the prosthesis 100 to a selected, ancillary pylon 130 or the like.

The foot portion 112, as best shown in FIG. 10 of the drawings, includes a toe section 124, an arch section 126, and a heel section 128. The heel section 128 has its rearward extremity 156 extending beyond the extreme rearward surface 158 of the attachment section 118 of the prosthesis 100. Mating bores, not shown, in the arch section 126 of the foot portion 112 and the ankle portion 114 receive respective bolt and nut combinations 116 to provide for assembling and disassembling of the foot and ankle portions 112 and 114. In the preferred embodiment, the various sections of the foot portion 112 are all constructed without the necessity of tapering of the thickness thereof, although those skilled in the art will understand that the invention is not limited to such non-tapering construction. If desired, optional pads 148 may be secured to the underside of the foot portions 114 at the toe and heel sections thereof to cushion the foot during walking and to create a profile for the bottom of the prosthesis 10 which corresponds to the interior of a shoe. Such a profile orients the foot 10, when the foot is in an unstressed state, at an appropriate angle for wearing shoes.

Figure 7:
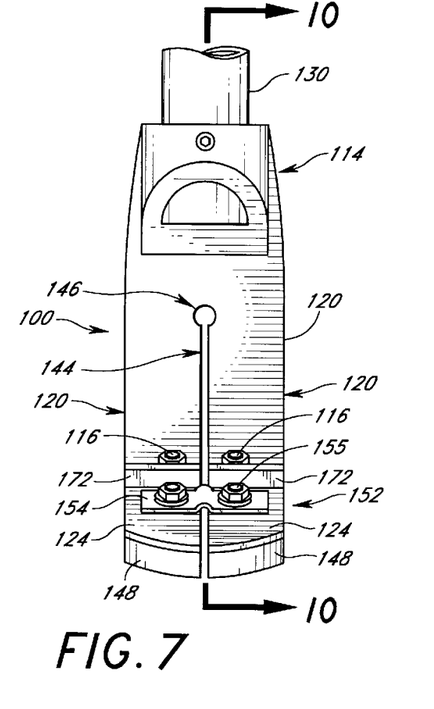
FIG. 7 is a front elevation view of an alternative embodiment of a prosthesis constructed in accordance with the invention.
Figure 8:
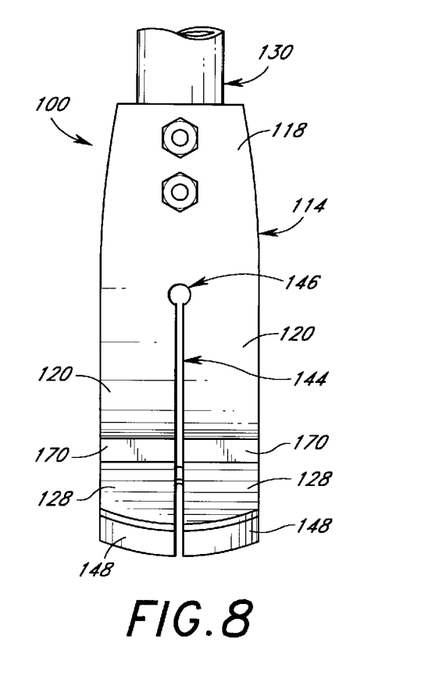
FIG. 8 is a rear elevation view of the prosthesis of FIG. 7.
Figure 11:
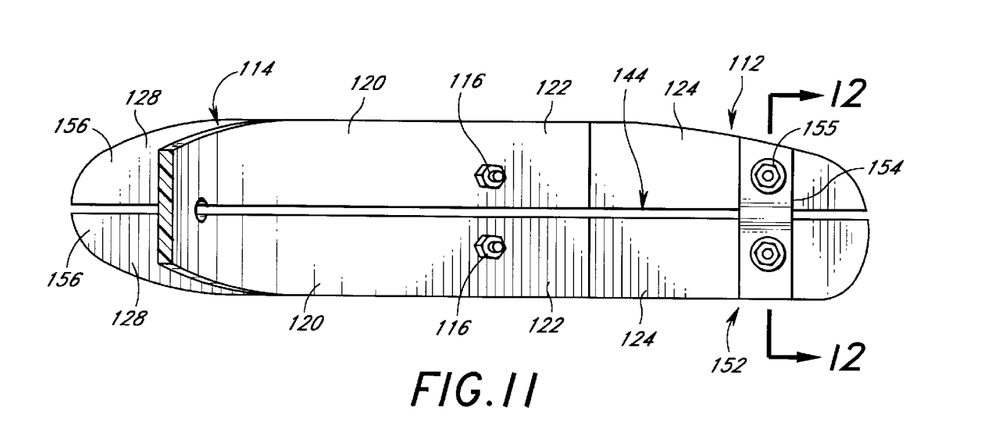
FIG. 11 is a partially sectional plan view of the prosthesis of FIG. 7 taken along line 11—11 of FIG. 9.
Figure 12:
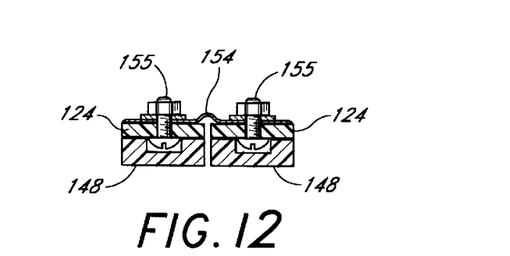
FIG. 12 is a sectional view of the prosthesis of FIG. 7, taken along line 12—12 of FIG. 11.

As illustrated in the accompanying FIGS. 7, 8 and 11, the foot portion 112 is preferably bifurcated into two foot portions, as shown, although additional multiple portions (not shown) may be beneficially provided and utilized without departing from the scope of my invention. Such bifurcation or further division may be accomplished through the incorporation of a slot 144 along the complete or substantially the complete length of the foot portion 112 and/or part of the ankle portion 114. Such a slot 144 may be molded or subsequently cut into the prosthesis, or may be achieved by the juxtaposition of two or more completely separate foot portions 112, each of which would be operatively attached to the lower attachment section 112 of the ankle portion 114. If the slot 144 extends up into the ankle portion 114, stress relief means 146, such as a hole, is preferably provided at the upper end of the slot 144, to prevent undesired excessive loading and deterioration of the prosthesis at that location. Such a hole may be drilled or molded into the prosthesis 100, as desired.

Additionally, the preferred embodiment of my invention includes retaining or connecting means 152 such as a strap 154 operatively attached to selected sections of the foot portions 112 through the provision of nut, bolt and washer combinations 155 or the like. The strap 154 is preferably fabricated from impregnated canvas or other flexible, lightweight, tough material, and is located forward of the arch section 126. By providing some play in the strap 154 rather than utilizing a taut strap, the selected foot portions 112 may flex independently of each other while exposed to lateral loading conditions, but will flex in a coordinated manner after sufficient movement has occurred to draw the strap taut. Thus, in extreme lateral loading conditions, more than one foot portion 112 will function to absorb and exert energy and prevent overload of a single foot portion 112.

It will be obvious to those skilled in the art that a virtually infinite variety of forefoot portions 112 and ankle portions 114 may be fabricated, each having unique spring stress response characteristics determined by the configuration, composition and amount of the various component materials utilized therein. The aforementioned demountable connections of the heel portion to the forefoot portion therefore permits interchangeability of those portions to match the weight, stride and activity schedule of the wearer utilizing the prosthetic foot.

Again, those skilled in the art will understand that the pylon coupling 132 have been described hereinabove merely by way of example, and that many alternative attachment means are available and may be utilized without departing from the scope of the invention, including without limitation, temporary or permanent bonding using various adhesives, plugs, pyramid connectors and/or the like.

Interposed between the undersurface 162 of the ankle section 120 of the ankle portion 114 and an upper surface 164 of the heel section 128 is an optional resilient, spring-action function block 170 of wedge shaped configuration. The function block 170 determines the lever arm of the heel section 128 and also isolates the undersurface 162 of the ankle section 120 in the upper surface 164 of the heel section 128 from each other. The function block 170 may be fabricated from a wide variety of resilient materials, including natural and synthetic rubbers, or the like.

Similarly, a second optional spring action function block 172 of like shape and construction can be interposed between the undersurface 174 of the lower attachment section 122 of the ankle portion 114 and an upper surface 176 of the toe section 124 to determine the lever arm of the toe section 124 and isolate the under surface 174 of the lower attachment section 122 in the upper surface 176 of the toe section 124 from each other.

Materials from which the foot portion 112 and ankle portion 114 are fabricated are preferably such as to provide an energy storing resilience or spring-like effect. This is preferred because each engagement of the prosthesis 100 with an adjacent surface impresses compression, torsional and other loads upon the prosthesis 100 which must be stored within the prosthesis and then, dependent upon the stride of the wearer, reimpressed upon said surface to achieve a natural stride conforming ideally in all respects to the stride of the unimpaired limb of the wearer of the prosthesis 100.

Those skilled in the art will understand that auxiliary flexure members (not shown) such as those described and shown in my U.S. Pat. Nos. 5,181,932 and 5,037,444 (see FIG. 7 therein) may be efficaciously utilized in connection with any embodiment of the above-described invention, without departing from the scope of the teachings hereof.

The foot and ankle portions 112 and 114 are preferably molded as unitary components and carefully formed to provide for uniform absorption of stress imposed thereupon. The configuration of both portions 112 and 114 is of utmost importance and the laminates of the polymer and polymers from which the portions 112 and 114 are fabricated must be resilient and capable of absorbing the compressive, torsional and other stresses referred to hereinabove and of restoring the stored energy created by such stresses, in a natural manner, to the impacted surface which originally imposed such stresses upon the prosthesis 100.

It has been found that there is a limited number of polymers capable of sustaining significant stresses in repetitive loads imposed upon the prosthesis 100, particularly in light of the countless numbers of cycles to which the prosthesis 100 is subjected during normal, every day use. At present, the best materials for the prosthesis are a composite of high strength graphite fiber in a toughness epoxy thermosetting resin system. There are several reasons for this: (1) high strength; (2) stiffness to weight ratio of graphite as compared to other materials; (3) the almost complete return of input or stored energy; (4) light weight; (5) high fatigue strength; (6) minimal creep. An alternative material, fiberglass/epoxy is a fair choice, but it is not as good as graphite because of lower fatigue strength and higher density. Kevlar is even less acceptable due to poor compression and shear strength, although it is the lowest density of those mentioned.

The function blocks 170 and 172 can be provided in different sizes and the materials having different compression characteristics so that the respective lever arms and the corresponding deflections of the heel section 128 and the toe section 124 may be increased or decreased as desired.

The ankle section 120 is preferably formed integrally with the upper attachment section 118 and said attachment section constitutes the upper extremity of the ankle section 120, while the initiation of lower attachment section 122 of the ankle portion 112 constitutes the lower extremity of the ankle section 120. The configuration of the ankle section 120 allows compressive loads to be imposed during impingement of the foot and ankle portions 112 and 114 upon an adjacent surface are absorbed and subsequently reimposed upon said surface. The ankle portion 120 is preferably designed so that it functions, substantially as an ankle joint to permit pivoting of the foot portion 112 thereabout in a manner analogous to the manner in which the normal foot pivots at the normal ankle joint on an axis transversely of said ankle joint.

It should be noted that the arch section 126 of each foot portion 112 is preferably substantially rigid and that the initial deflection of each heel section 128 occurs immediately adjacent or rearward of extremity 156 of said heel section, terminating immediately adjacent the function block 170. Obviously, a greater length or less resilient function block 170 reduces the lever arm of the heel section 128 of each foot portion 112 and correspondingly reduces the modulus of deflection of said ankle section, while a smaller length or more resilient function block 170 increases the lever arm and correspondingly increases the deflection of the heel section 128 under load. The length of the second function block 172 likewise affects the lever arm and deflection of the toe section 124 of each foot portion 112.

The toe section 124 and heel section 128 can be provided in different lengths to correspond with the size of the foot of the wearer of the prosthesis 100. When such different lengths are provided, corresponding reduction or increase in the number of laminae and thickness of taper of the respective toe sections 124 and heel sections 128 can be made to provide for the proper flexure of said toe and ankle sections. It should also be noted that, even with the shortest heel section 128 a rearward extremity 156 thereof preferably projects beyond the rearward surface 58 of the ankle portion 114. Consequently, the stabilizing and stress absorption characteristics of the heel section 128 of the prosthesis 100 are always maintained.

The prosthesis of my invention has been described with some particularity but the specific designs and constructions disclosed are not to be taken as delimiting of the invention in that various obvious modifications will at once make themselves apparent to those of ordinary skill in the art, and which will not depart from the essence of the invention as defined by a fair reading of the appended claims.

What is claimed is:

1. A foot prosthesis for supporting an amputee relative to a support surface, said foot prosthesis comprising:

a first prosthetic support member configured to provide energy storage and release and having an upper attachment section and a lower attachment section; and a second prosthetic support member attached to the lower attachment section of said first support member;

said first and second prosthetic support members each having multiple flexing portions configured to flex substantially independently of one another substantially completely along their length, said flexing portions being defined by one or more slots extending completely through said second prosthetic support member along the entire length thereof and through at least the lower attachment section of said first prosthetic support member whereby resilient inversion and eversion support is thereby provided.

2. The foot prosthesis of claim 1, wherein said one or more slots extend substantially completely through the lower attachment section of said first prosthetic support member and terminate at a point between said upper attachment section and said lower attachment section.

3. The foot prosthesis of claim 1, wherein said independently flexing portions are substantially symmetric with one another.

4. The foot prosthesis of claim 1, wherein said first and second prosthetic support members are fabricated from superimposed laminates maintained in operative relationship by an encapsulating polymer.

5. The foot prosthesis of claim 1, wherein said first prosthetic support member further comprises a resilient ankle section disposed between said upper and lower attachment sections.

6. The foot prosthesis of claim 5, wherein said first prosthetic support member further comprises a toe section disposed at an anterior distal end thereof.

7. The foot prosthesis of claim 1, wherein said second prosthetic support member comprises a heel section.

8. The foot prosthesis of claim 7, wherein said second prosthetic support member is demountably secured to the lower attachment section of said first prosthetic support member.

9. The foot prosthesis of claim 7, wherein said second prosthetic support member is secured to the lower attachment section of said first prosthetic support member using an adhesive.

10. The foot prosthesis of claim 9, wherein said second prosthetic support member is secured to the lower attachment section of said first prosthetic support member using an intermediate resilient member.

11. A foot prosthesis for supporting an amputee relative to a support surface, said foot prosthesis comprising:
an upper attachment section configured to secure said foot prosthesis to a socket or pylon;
a plurality of first support members having distal ends and extending generally downward and forward from said upper attachment section defining a lower attachment section, said first support members being separated from each other at said distal ends of said first support members, said first support members being substantially separated from one another along their length so as to enable each to move substantially independently of the others; and
a plurality of second support members having distal ends, said second support members being attached to the lower attachment section and extending substantially anteriorly and posteriorly therefrom, said posterior extension of said second support members forming a plurality of rearward ends at about the location of a heel of a natural human foot, said rearward ends being configured to flex substantially independently of one another, said second support members being separated from each other at said distal ends of said second support members, said second support members being substantially separated from one another along their length so as to enable each to move substantially independently of the others.

12. The foot prosthesis of claim 11, wherein said plurality of first and second support members are substantially symmetric with one another about a plane of separation.

13. The foot prosthesis of claim 11, wherein said plurality of first and second support members are formed from sheet-like members having substantially uniform or slightly tapering rectangular cross-sections and which are curved and shaped to form said first and second support members.

14. The foot prosthesis of claim 11, wherein said plurality of first and second support members are fabricated from superimposed laminates maintained in operative relationship by an encapsulating polymer.

15. The foot prosthesis of claim 11, wherein said plurality of first support members comprise a resilient ankle section.

16. The foot prosthesis of claim 15, wherein said plurality of first support members further comprise toe sections disposed at said distal ends thereof.

17. The foot prosthesis of claim 11, wherein said plurality of second support members comprise heel sections.

18. A foot prosthesis for supporting an amputee relative to a support surface, said foot prosthesis comprising:
an ankle section configured to store and release walking energy and including an upper attachment section configured to secure said foot prosthesis to a socket or other prosthetic device and a lower attachment section;
a toe section extending generally anteriorly from said ankle section; and
a heel section extending generally posteriorly from said ankle section;
said ankle, toe, and heel sections being substantially non-rotatably secured to one another at said lower attachment section and being further divided into at least two longitudinal forefoot members separated by a gap extending substantially completely along the length of said foot prosthesis from the anterior-most tip of said toe section through said attachment section and the posterior-most tip of said heel section, said longitudinal forefoot members being configured to flex substantially independently of one another substantially completely along their length.

19. The foot prosthesis of claim 18 wherein said ankle section and said heel section are demountably secured to one another such that they may be readily removed and replaced with similar sections having different size or spring rate to suit the size, stride, height, weight and/or activity level of an amputee wearing said foot prosthesis.

20. The foot prosthesis of claim 18, wherein said ankle, toe, and heel sections are demountably secured to one another using nut and bolt members.

21. The foot prosthesis of claim 18, wherein said ankle, toe and heel sections are secured at said lower attachment section using an adhesive.

22. The foot prosthesis of claim 18, further comprising an intermediate resilient member disposed between said heel and ankle sections and/or said toe and ankle sections.

23. A foot prosthesis for supporting an amputee relative to a support surface, said foot prosthesis comprising:
a first prosthetic support member configured to provide energy storage and release and having an upper attachment section and a lower attachment section; and
a second prosthetic support member attached to the lower attachment section of said first support member;
said first and second prosthetic support members each having multiple independently flexing portions defined by one or more slots extending substantially completely along the length of said second prosthetic support member and at least the lower attachment section of said first prosthetic support member whereby resilient inversion and eversion support is thereby provided, said first and second prosthetic support members being fabricated from superimposed laminates maintained in operative relationship by an encapsulating polymer.

24. A foot prosthesis for supporting an amputee relative to a support surface, said foot prosthesis comprising:

a first prosthetic support member configured to provide energy storage and release and having an upper attachment section and a lower attachment section; and a second prosthetic support member attached to the lower attachment section of said first support member;

said first and second prosthetic support members each having multiple independently flexing portions defined by one or more slots extending substantially completely along the length of said second prosthetic support member and at least the lower attachment section of said first prosthetic support member whereby resilient inversion and eversion support is thereby provided, said second prosthetic support member comprising a heel section and being secured to the lower attachment section of said first prosthetic support member using an adhesive.

25. The foot prosthesis of claim 24, wherein said second prosthetic support member is secured to the lower attachment section of said first prosthetic support member using an intermediate resilient member.

26. A foot prosthesis for supporting an amputee relative to a support surface, said foot prosthesis comprising:

an ankle section configured to store and release walking energy and including an upper attachment section configured to secure said foot prosthesis to a socket or other prosthetic device and a lower attachment section;

a toe section extending generally anteriorly from said ankle section; and a heel section extending generally posteriorly from said ankle section;

said ankle, toe, and heel sections being substantially non-rotatably secured to one another at said lower attachment section and being further divided into at least two longitudinal forefoot members separated by a gap extending substantially completely through said foot prosthesis from the anterior-most tip of said toe section through said attachment section and the posterior-most tip of said heel section, said ankle section and said heel section being demountably secured to one another such that they may be readily removed and replaced with similar sections having different size or spring rate to suit the size, stride, height, weight and/or activity level of an amputee wearing said foot prosthesis.

27. A foot prosthesis for supporting an amputee relative to a support surface, said foot prosthesis comprising:

an ankle section configured to store and release walking energy and including an upper attachment section configured to secure said foot prosthesis to a socket or other prosthetic device and a lower attachment section;

a toe section extending generally anteriorly from said ankle section; and a heel section extending generally posteriorly from said ankle section;

said ankle, toe, and heel sections being substantially non-rotatably secured to one another at said lower attachment section and being further divided into at least two longitudinal forefoot members separated by a gap extending substantially completely through said foot prosthesis from the anterior-most tip of said toe section through said attachment section and the posterior-most tip of said heel section, said ankle, toe, and heel sections being demountably secured to one another using nut and bolt members.

28. A foot prosthesis for supporting an amputee relative to a support surface, said foot prosthesis comprising:

an ankle section configured to store and release walking energy and including an upper attachment section configured to secure said foot prosthesis to a socket or other prosthetic device and a lower attachment section;

a toe section extending generally anteriorly from said ankle section; and a heel section extending generally posteriorly from said ankle section;

said ankle, toe, and heel sections being substantially non-rotatably secured to one another at said lower attachment section and being further divided into at least two longitudinal forefoot members separated by a gap extending substantially completely through said foot prosthesis from the anterior-most tip of said toe section through said attachment section and the posterior-most tip of said heel section, said ankle, toe, and heel sections being secured at said lower attachment section using an adhesive.

* * * * *